(12) United States Patent
Schipke (10) Patent No.: US 12,264,792 B2
(45) Date of Patent: Apr. 1, 2025

(54) SYSTEMS, METHODS, AND DEVICES FOR SPECTROCHROME LASER OUTPUT

(71) Applicant: Kimberly Schipke, Tupelo, MS (US)

(72) Inventor: Kimberly Schipke, Tupelo, MS (US)

( * ) Notice: Subject to any disclaimer, the term of this patent is extended or adjusted under 35 U.S.C. 154(b) by 552 days.

(21) Appl. No.: 17/807,331

(22) Filed: Jun. 16, 2022

(65) Prior Publication Data

US 2023/0006406 A1    Jan. 5, 2023

Related U.S. Application Data (60) Provisional application No. 63/211,780, filed on Jun. 17, 2021.

(51) Int. Cl.
| | | |
|---|---|---|
| *F21L 4/00* | (2006.01) | |
| *F21V 3/06* | (2018.01) | |
| *F21V 23/04* | (2006.01) | |
| *F21Y 115/30* | (2016.01) | |

(52) U.S. Cl.
CPC ............... *F21L 4/005* (2013.01); *F21V 3/06* (2018.02); *F21V 23/0414* (2013.01); *F21Y 2115/30* (2016.08)

(58) Field of Classification Search
CPC ...................................................... F21L 4/005
See application file for complete search history.

(56) References Cited

U.S. PATENT DOCUMENTS

| | | | | |
|---|---|---|---|---|
| 2,307,379 | A | * | 1/1943 | Armstrong ................ F21L 4/00 359/228 |
| 5,165,781 | A | * | 11/1992 | Orak ....................... G09F 19/12 362/186 |
| 2004/0120143 | A1 | * | 6/2004 | Chen .................... F21V 33/0056 362/202 |
| 2010/0283264 | A1 | * | 11/2010 | Rastegar .............. H02K 7/1876 290/1 R |

FOREIGN PATENT DOCUMENTS

| | | | | |
|---|---|---|---|---|
| WO | WO-2007096814 | A1 | * 8/2007 | ................ F21L 4/00 |
| WO | WO-2018097755 | A1 | * 5/2018 | |

* cited by examiner

*Primary Examiner* — Zheng Song
(74) *Attorney, Agent, or Firm* — McDonnell Boehnen Hulbert & Berghoff LLP (57) ABSTRACT

In one aspect, an example handheld device for providing a spectrochrome output includes (a) an enclosed chamber containing one or more substances; (b) a light source; (c) an electromagnetic coil; (d) one or more magnets; and (e) a housing, wherein the housing is configured to: (i) secure the enclosed chamber; (ii) secure the light source such that an output of the light source is substantially aligned to pass through the enclosed chamber in one or more directions; and (iii) secure the electromagnetic coil around the enclosed chamber such that an electromagnetic field is created in a substantially same direction of the output of the light source through the enclosed chamber.

21 Claims, 6 Drawing Sheets

SYSTEMS, METHODS, AND DEVICES FOR SPECTROCHROME LASER OUTPUT

RELATED APPLICATION

This application claims priority to U.S. Provisional Application No. 63/211,780 filed Jun. 17, 2021, which is incorporated herein by reference in its entirety.

USAGE AND TERMINOLOGY

In this disclosure, unless otherwise specified and/or unless the particular context clearly dictates otherwise, the terms "a" or "an" mean at least one, and the term "the" means the at least one.

SUMMARY

In one aspect, an example handheld device for providing a spectrochrome output is disclosed. The example handheld device includes (a) an enclosed chamber containing one or more substances; (b) a light source; (c) an electromagnetic coil; (d) one or more magnets; and (e) a housing, wherein the housing is configured to: (i) secure the enclosed chamber; (ii) secure the light source such that an output of the light source is substantially aligned to pass through the enclosed chamber in one or more directions; and (iii) secure the electromagnetic coil and the one or more magnets around the enclosed chamber such that an electromagnetic field is created in a substantially same direction of the output of the light source through the enclosed chamber.

BRIEF DESCRIPTION OF THE FIGURES

The above, as well as additional, features will be better understood through the following illustrative and non-limiting detailed description of example embodiments, with reference to the appended drawings.

DETAILED DESCRIPTION

I. Overview

Light and electromagnetic waves can be used in a number of ways to help amplify and interact with a number of substances. These interactions may impart unexpected results in the medium through which the light may pass, including human tissues and digestible liquids (e.g., water). To date, there have not been any consistent, convenient, and/or portable options for practitioners incorporating such light waves (including lasers) and/or electromagnetic waves into their practice for treating human conditions.

Conventionally, utilizing such light waves (including lasers) and/or electromagnetic waves has required large scale systems, which may vary from practitioner to practitioner, and may cause different treatment results from patient to patient.

If, however, practitioners could provide an efficient, effective, and novel solution for consistent, convenient, and/or portable options for practitioners incorporating such light waves (including lasers) and/or electromagnetic waves into their practice for treating human conditions, then the overall variability associated with these treatments would be reduced.

Accordingly, features of the present disclosure can help to address these and other issues to provide an improvement to select technical fields. More specifically, features of the present disclosure help address issues within and provide improvements for select technical fields, which include for example, handheld devices that include passing a light source through an enclosed chamber containing one or more substances and surrounded by an electromagnetic coil, such that an output of the light source is substantially aligned to pass through the enclosed chamber in one or more directions and an electromagnetic field is created in a substantially same direction of the output of the light source through the enclosed chamber. These features will now be described in the claims below.

Embodiments of the present invention provide methods, systems, and devices that allow practitioners to effectively use light waves (including lasers) and/or electromagnetic waves into their practice for a number of reasons, including treating human physical and mental health conditions.

More specifically, example embodiments relate to methods, systems, and devices for improving the consistency, ease, and performance treatments using light waves (including lasers) and/or electromagnetic waves.

A handheld device for providing a spectrochrome output may include an enclosed chamber containing one or more substances. In some example embodiments, these substances may include one or more substances that are in a solid, gaseous, or liquid phase, or some combination thereof. For example, in some embodiments, the enclosed chamber may contain one or more noble gases, including one or more of the following gases: (i) helium; (ii) neon; (iii) argon; (iv) krypton; (v) xenon; and (vi) radon. In other examples, the enclosed chamber may contain one or more of the following non-noble gases: hydrogen, nitrogen, oxygen, fluorine, and chlorine, potentially in combination with other substances (including the noble gases listed above). In a further aspect, the enclosed chamber may also contain one or more solid and/or liquid materials (including solid and/or liquid versions of the substances listed above), among other possibilities.

In a further aspect, the handheld device for providing a spectrochrome output may also include a light source. This light source may include one or more of several different types of light from a variety of sources. For example, in some embodiments, the light source may be a laser. In a further aspect, the laser may operate at one or more wavelengths and create a visible output of one or more colors, including one or more of the following: (i) a laser with a wavelength between approximately 520 to 560 nanometers and a visible output of green light; (ii) a laser with a wavelength of approximately 380 to 450 nanometers and a visible output of violet light; (iii) a laser with a wavelength between approximately 450 to 495 nanometers and a visible output of blue light; (iv) a laser with a wavelength between approximately 495 to 520 nanometers and a visible output of cyan light; (v) a laser with a wavelength between approximately 560 to 590 nanometers and a visible output of yellow light; (vi) a laser with a wavelength between approximately 590 to 620 nanometers and a visible output of orange light; and (vii) a laser with a wavelength between approximately 620 to 740 nanometers and a visible output of red light. Other examples are possible.

In other examples, the light source may include light generated by one or more other light sources, including one or more of the following: (i) a fluorescent light source; (ii) light-emitting diode light source; (iii) halogen light source; (iv) a filament light source; and (v) reflector and/or refractor directing light from external light sources (e.g., the sun).

In a further aspect, the handheld device for providing a spectrochrome output may also include an electromagnetic coil. This electromagnetic coil may be made of and/or include one or more of several different materials and arranged in a variety of ways. For example, in some embodiments, the electromagnetic coil may be made of one or more of the following: (i) copper wire; (ii) silver wire; (iii) gold wire; (iv) aluminum wire; (v) iron wire, and/or combinations thereof.

In a further aspect, the electromagnetic coil may be arranged in a variety of ways, including wrapping the electromagnetic coil around the enclosed chamber or a receiving portion of the handheld device that holds the enclosed chamber, either of which may be configured in a manner that may create a field substantially in the center of the coil and the enclosed chamber. For example, the electromagnetic coil may be a continuous strand of wire wrapped uniformly around the enclosed chamber a receiving portion of the handheld device that holds the enclosed chamber such that the electromagnetic field created by the electromagnetic coil is focused on an area in the enclosed chamber. To do so, the handheld device may also contain one or more magnets. In some examples, these magnets may include one or more of the following: (i) neodymium magnets (including neodymium iron boron ("NdFeB") magnets); (ii) ceramic magnets; (iii) ferrite magnets; (iv) samarium cobalt ("SmCo") magnets; and (v) alnico magnets. Other examples are possible.

In a further aspect, in other examples, the electromagnetic coil may be a continuous strand of wire wrapped uniformly around the enclosed chamber such that a magnetic field created by the electromagnetic coil is focused on an area in the enclosed chamber. In some examples, an electrical current may be applied to the electromagnetic coil to create a magnetic field. To create this field, one or more electrical currents may be applied to the electromagnetic coil using one or more sources (e.g., one or more batteries). Other examples are possible.

In a further aspect, the handheld device for providing a spectrochrome output may also include a housing that may be made of one or more materials and be configured to promote one or more functionalities of the handheld device. In some examples, this housing may be made of and/or include one or more of several different materials, including plastics, rubbers, metals, glass, and/or combinations thereof, as well as other materials. Furthermore, this housing may be arranged in a variety of ways. For example, in some embodiments, the housing may be configured to secure the enclosed chamber that holds the enclosed chamber (e.g., via a receiving portion of the housing), perhaps in one or more directions in relation to other components of the handheld device. For example, the housing may be configured to secure the light source such that an output of the light source is substantially aligned to pass through the enclosed chamber in one or more directions. In other examples, the housing may be configured to secure the electromagnetic coil and the one or more magnets around the enclosed chamber such that an magnetic field is created in a substantially same direction of the output of the light source through the enclosed chamber.

In a further aspect, the housing may have one or more recesses to align the electromagnetic coil and the one or more magnets around the enclosed chamber such that the magnetic field is created in a substantially same axial direction of the output of the light source through the enclosed chamber. In other examples, the housing may have one or more recesses to hold one or more other more specific components of the handheld device (e.g., one or more recesses to hold particular types of neodymium magnets).

In a further aspect, the housing may be configured to receive the light source and/or after receiving the light source, activate the light source by turning the light source in a clockwise and/or counterclockwise manner in relation to the housing (e.g., using one or more specifically configured receiving portions of the housing and/or keys).

In a further aspect, the components described herein may work together to create one or more unexpected results. For example, the electromagnetic coil (e.g., the wiring and magnets) interacts with the electromagnetic aspects of the light emitted from the light source. For example, the magnetic aspect interacts with the light as it passes through the electromagnetic coils and the electric aspect interacts with the light as it passes by the magnets. In a further aspect, the magnets may have opposite poles pointing towards each other so they are trying to attract each other. In yet a further aspect, the light emitted by the light source (e.g., the laser) may act as a carrier wave for the one or more materials contained in the enclosed chamber (e.g., the stable noble gas argon contained in the enclosed chamber).

In a further aspect, the type of light emitted from the light source may influence the light that emits from the handheld device after passing through the enclosed chamber. For example, if visibly green light is utilized, the output may be perceived as a neutralizing color and, when used on a patient's body (e.g., tissue, organs, bones, teeth, gums, etc.), if the electromagnetic charge is too high or too low then it can stimulate or depress areas which might be out of balance. Put another way, if the patient feels emotionally charged then it can help neutralize those emotions (e.g., to help address mental and emotional trauma). Other examples are possible.

For example, the light ultimately emitted from the handheld device may be used to charge a glass of drinking water, bath water, and/or any type of water with which a patient may interact. Other examples are possible.

Figure 1A:
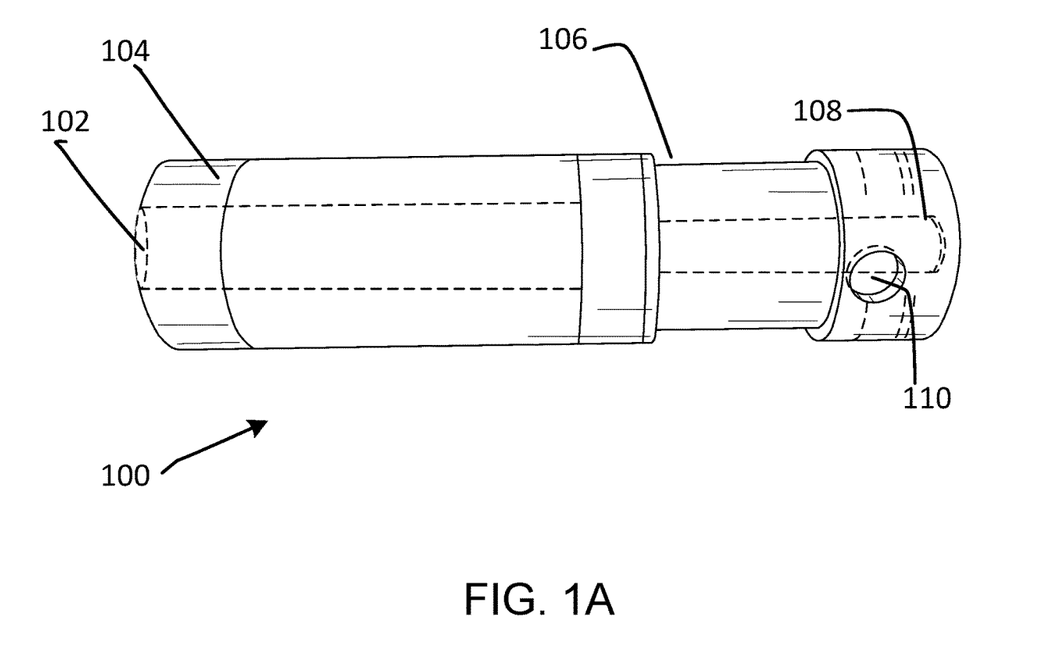
FIG. 1A illustrates the spectrochrome housing, according to an example embodiment.

Referring now to the figures, FIG. 1A illustrates a spectrochrome housing 100. As shown in FIG. 1A, in this example embodiment, the spectrochrome housing 100 has a first receiving portion 102; an engaging mechanism 104 (e.g., for a light source); a first recess 106; a second receiving portion 108; and a second recess 110. In some embodiments, the spectrochrome housing 100 may be made of and/or include one or more of several different materials, including plastics, rubbers, metals, glasses, and/or combinations thereof, as well as other materials.

In some embodiments, the first receiving portion 102 may be configured to receive a light source. This light source may include one or more of several different types of light from a variety of sources.

For example, in some embodiments, the light source may be a laser. In a further aspect, the laser may operate at one or more wavelengths and create a visible output of one or more colors, including one or more of the following: (i) a laser with a wavelength between approximately 520 to 570 nanometers and a visible output of green light; (ii) a laser with a wavelength of approximately 380 to 450 nanometers and a visible output of violet light; (iii) a laser with a wavelength between approximately 450 to 500 nanometers and a visible output of blue light; (iv) a laser with a wavelength between approximately 500 to 520 nanometers and a visible output of cyan light; (v) a laser with a wavelength between approximately 570 to 590 nanometers and a visible output of yellow light; (vi) a laser with a wavelength between approximately 590 to 620 nanometers and a visible output of orange light; and (vii) a laser with a wavelength between approximately 625 to 740 nanometers and a visible output of red light. In some embodiments, the light source may include lasers that emit light that includes wavelengths not in the visible part of the light spectrum. Other examples, are possible.

For example, the light source may include light generated by one or more other light sources, including one or more of the following: (i) a fluorescent light source; (ii) light-emitting diode light source; (iii) halogen light source; (iv) a filament light source; and (v) reflector and/or refractor directing light from external light sources (e.g., the sun).

The engaging mechanism 104 may interact with the light source in such a way that a substantial portion of the light from the light source passes through the spectrochrome housing 100 and leaves through the second receiving portion 110. Further, in some embodiments, an interior wall of the engaging mechanism 104 can change in thickness, such that the engaging mechanism 104 can be used to activate the light source through a manual manipulation, for example, a counterclockwise and/or counterclockwise rotation of the housing 100 in relation to the light source that may be inserted into the housing (e.g., via the first receiving portion 102).

In some embodiments, the first recess 106 can be surrounded with an electromagnetic coil. Further, in some embodiments, the second recess 108 can be filled with a magnet. In some embodiments there can be one, two, or multiple second recesses 108 to receive one, two, or multiple magnets of the same or different magnetic strengths.

In some embodiments, the second receiving portion 110 can receive an enclosed chamber containing one or more substances that are in a solid, gaseous, or liquid phase, or some combination thereof. Other examples, are possible.

Figure 1B:
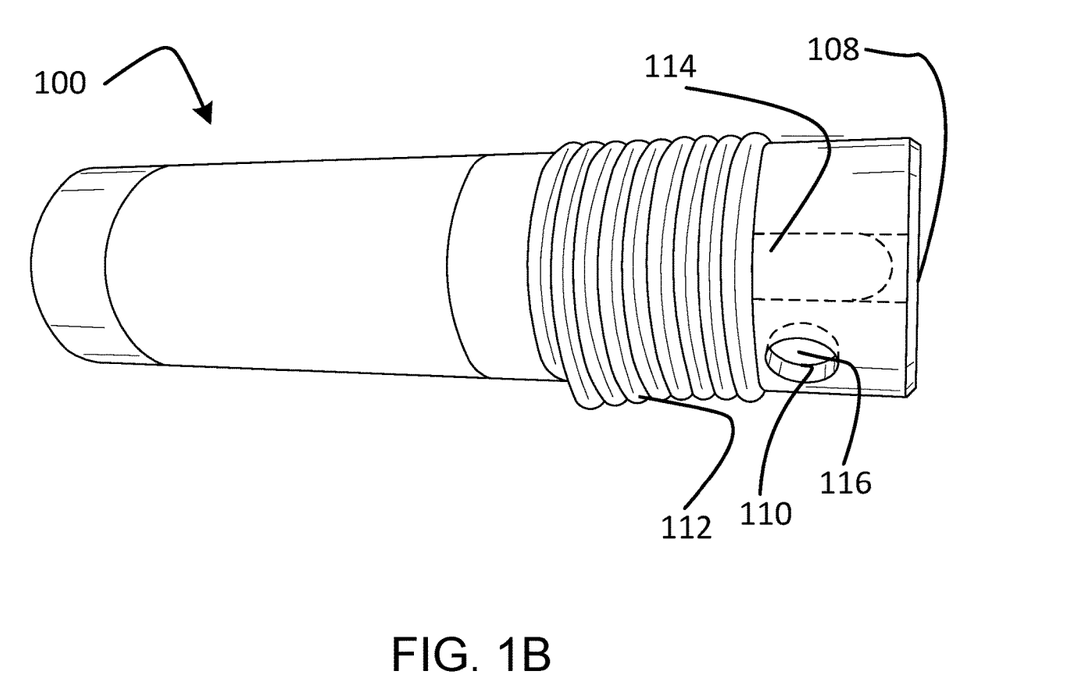
FIG. 1B illustrates an assembled view of the spectrochrome housing, according to an example embodiment.

Turning to FIG. 1B, FIG. 1B shows an assembled view of an example embodiment of the spectrochrome housing 100. As shown in FIG. 1B, the assembled view of the spectrochrome housing 100 includes an electromagnetic coil 112, and an enclosed chamber 114 inserted into the second receiving portion 110, and a magnet 116 inserted into the second recess 108.

In some embodiments, the electromagnetic coil 112 is wrapped around the first recess 106. In some embodiments, the electromagnetic coil 112 may be made of and/or include one or more of several different materials and arranged in a variety of ways. For example, in some embodiments, the electromagnetic coil 112 may be made of one or more of the following: (i) copper wire; (ii) silver wire; (iii) gold wire; (iv) aluminum wire; or (v) iron wire. In a further aspect, the electromagnetic coil 112 may be arranged in a variety of ways, including wrapping the electromagnetic coil 112 around the first recess 106 and around the enclosed chamber 114 in a manner that may create a magnetic field substantially in the center of the enclosed chamber 114. For example, the electromagnetic coil 112 may be a continuous strand of wire wrapped uniformly around the enclosed chamber 114 such that the magnetic field created by applying a current to the electromagnetic coil 112 is focused on an area in the enclosed chamber 114. The current can be generated using one or more sources (e.g., one or more batteries). Other examples are possible, including creating a magnetic field in different sections of the enclosed chamber 114. In some example embodiments, the electromagnetic coil 112 may be insulated on an exterior portion (e.g., the exterior portion of the spectrochrome housing 100) and/or between the electromagnetic coil 112 and the first recess 106, among other possibilities. The types of materials used to insulate the electromagnetic coil 112 may include one or more of the following materials: (i) rubbers, (ii) polyvinyl chloride (PVC), (iii) polyethylene, (iv) nylon, (v) silicon, (vi) Teflon, and/or combinations thereof. Other examples are possible.

In some embodiments, the enclosed chamber 114 may be filled with one or more substances that are in a solid, gaseous, or liquid phase, or some combination thereof. For example, in some embodiments, the enclosed chamber 114 may contain gases individually or as a combination, including one or more of the following gases: (i) helium; (ii) neon; (iii) argon; (iv) krypton; (v) xenon; (vi) radon; (vii) hydrogen; (viii) nitrogen; (ix) oxygen; (x) fluorine; and (xi) chlorine. In a further aspect, the enclosed chamber 114 may also contain one or more solid and/or liquid materials (including solid and/or liquid versions of the substances listed above), among other possibilities.

In some embodiments, the one or more magnets 116 may include one or more of the following: (i) neodymium magnets (including neodymium iron boron ("NdFeB") magnets); (ii) ceramic magnets; (iii) ferrite magnets; (iv) samarium cobalt ("SmCo") magnets; and (v) alnico magnets. Other examples are possible. In embodiments where there is more than one magnet 116, the magnetic fields created by the magnets can be oriented in the same or different directions to change the strength and direction of the magnetic field within the enclosed chamber 114.

The magnetic fields produced by the electromagnetic coil 112 and the one or more magnets 116 and combine to change the magnetic field within the enclosed chamber 114. In a further aspect, the magnetic field may interact with the light emitted from the light source as it passes through the enclosed chamber 114.

Figure 2A:
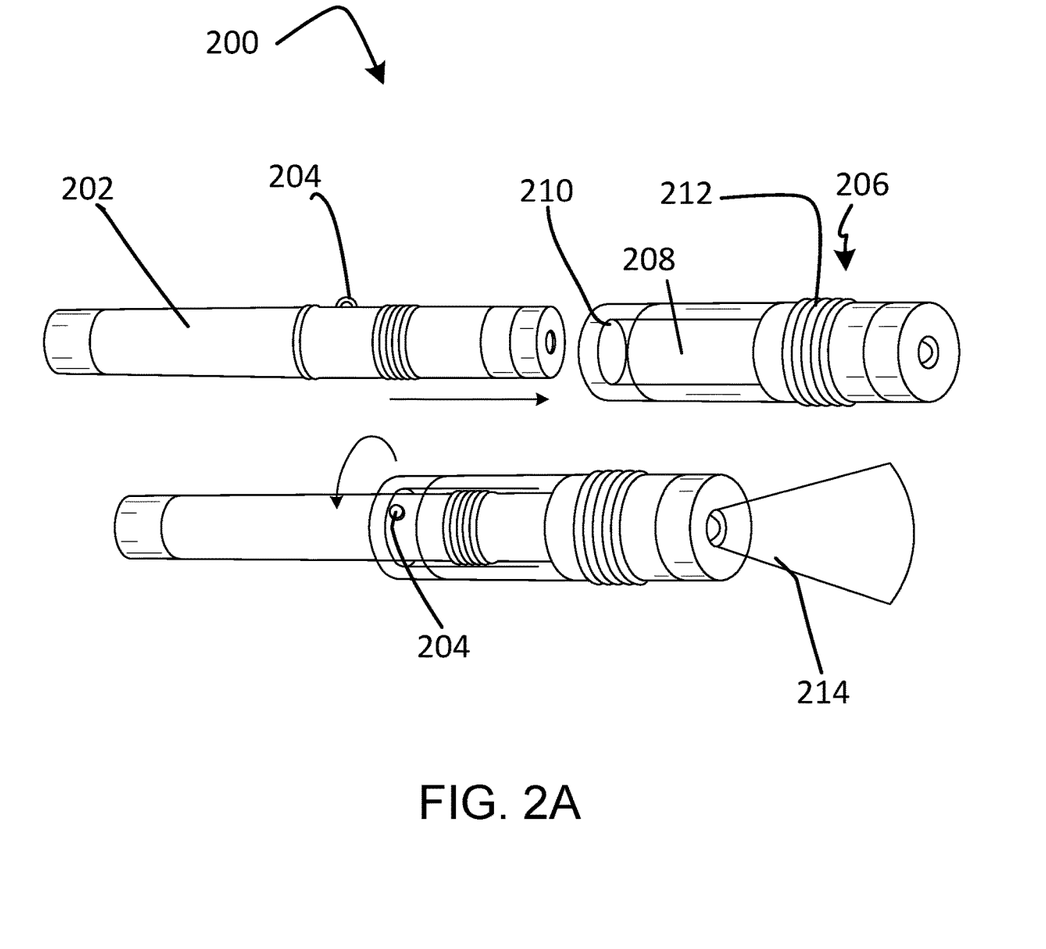
FIG. 2A illustrates a handheld device including a spectrochrome housing, light source, and electromagnetic coil, according to an example embodiment in both decoupled and assembled views.

Turning to FIG. 2A, the upper portion of FIG. 2A illustrates a decoupled view of various components of a handled device 200, while the lower portion of FIG. 2A illustrates an assembled view of the handheld device. The handheld device illustrated in FIG. 2A includes a light source 202, containing an activation mechanism 204, and a spectrochrome housing 206 with a first receiving portion 208 that contains an engaging mechanism 210 and an insulated electromagnetic coil 212. In example embodiments, when assembled, the combination of light source 202 and spectrochrome housing 206 can produce an emitted light 214.

For example, as shown in the bottom portion of FIG. 2A, in some embodiments, the engaging mechanism 204 aligns with the engaging mechanism 210 in the spectrochrome housing 206 to secure the light source 202 within the first receiving portion 208 of the spectrochrome housing 206. In a further aspect, the spectrochrome housing 206 may be configured to activate the light source 202 by turning the light source 202 in a clockwise and/or counterclockwise manner in relation to the spectrochrome housing 206 (e.g., using one or more specifically configured keys) can produce an emitted light 214. In example embodiments, Further, in some embodiments, an interior wall of the engaging mechanism 204 can vary in thickness, such that the engaging mechanism 204 can be used to activate the light source 202 through a manual manipulation, for example, a counterclockwise and/or counterclockwise rotation of the housing 206 in relation to the light source to activate the light source's activation mechanism 204 and produce the emitted light 214.

Figure 2B:
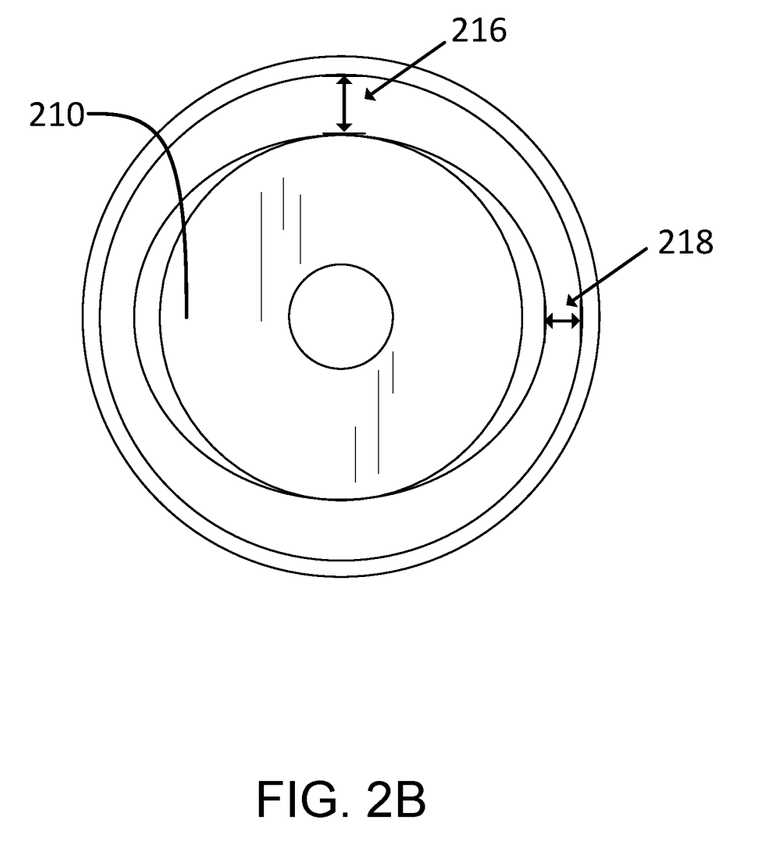
FIG. 2B illustrates a top down view of a first receiving portion of the spectrochrome housing of FIG. 2A.

For example, turning to FIG. 2B, FIG. 2B illustrates a top-down view of engaging mechanism 210, which contains an interior wall of a first thickness 216 and a second thickness 218. In FIG. 2B, first thickness 216 is great than second thickness 218, such that when the light source 202 is inserted into the first receiving portion of 208, the activation mechanism 204 aligns with the engaging mechanism 210, and a counterclockwise and/or counterclockwise rotation of the housing 206 in relation to the light source causes a thicker portion of the engaging mechanism 210 (e.g., first thickness 216) to compress the light source's activation mechanism 204 and produce the emitted light 214. Other examples are possible.

Figure 3A:
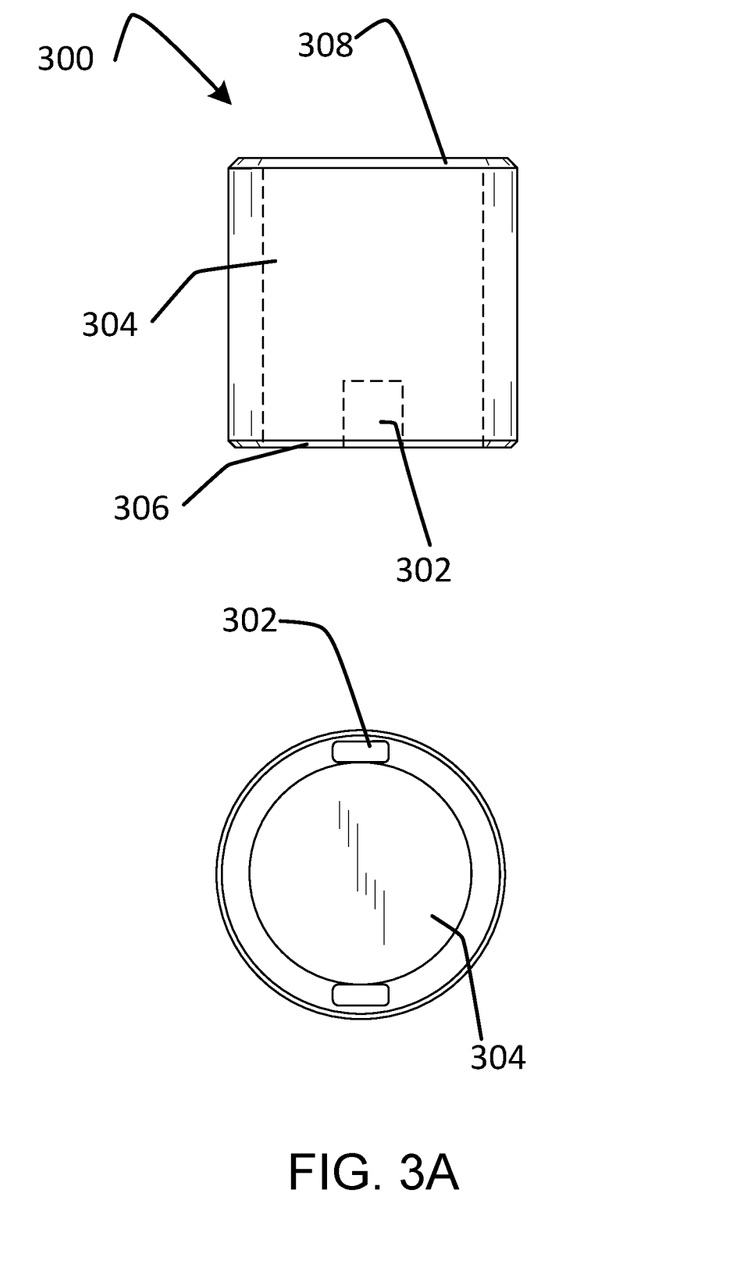
FIG. 3A illustrates a detailed view of a housing cap for use with any of the spectrochrome housings of FIGS. 1A-2B, according to an example embodiment.

Turning to FIG. 3A, the upper portion of FIG. 3A shows a detailed sagittal view of the housing cap 300 comprising a magnet recess 302, a receiving portion 304, a first end 306, and a second end 308. The lower portion of FIG. 3 shows an axial view of the housing cap 300. In some embodiments, as illustrated in FIG. 3A, the first end 306 may be open and may be configured to receive one or more components (e.g., a spectrochrome housing). In some embodiments, as illustrated in FIG. 3A, the second end 308 may be closed, and may be configured to hold one or more substances in the internal portion 304, particularly once one or more components (e.g. a spectrochrome housing) are inserted into the first end 306. Such substances may comprise one or more of the following: (i) water, (ii) gemstones, (iii) essential oils, (iv) salts, (v) homeopathic substances and remedies, (vi) pharmaceuticals, (vii) natural substances, and/or combinations thereof, among other substances. Other examples are possible.

In some embodiments, one or more magnets can be inserted into the recess 302. In some embodiments, there can be one, two, or multiple recesses 302 that can be filled with one two or multiple magnets of the same or different types and magnetic strengths. In embodiments were there are more than one magnet recess 302, the magnets may be oriented in the same or different directions to change the strength and direction of the magnetic field within the internal portion 304. Further, in example embodiments, the overall direction of the magnetic field can be aligned with the direction of the light moving through the housing cap 300.

Figure 3B:
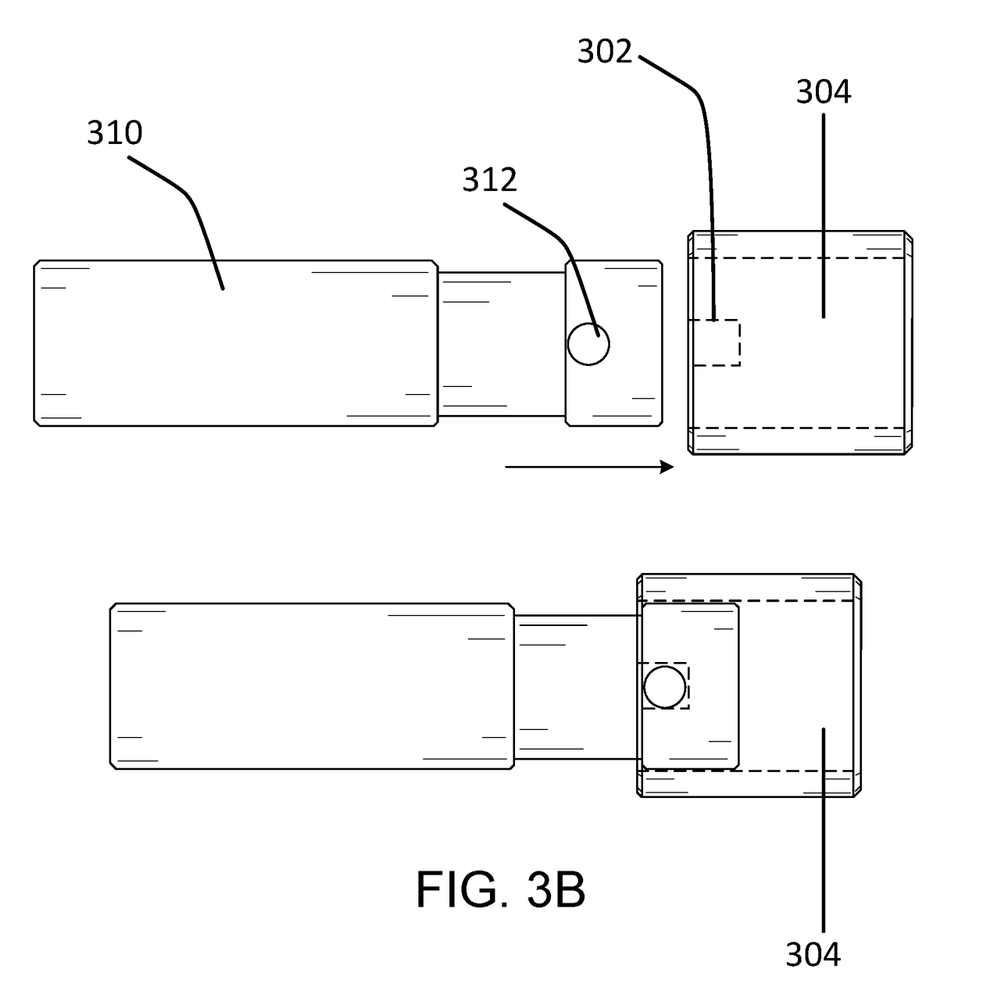
FIG. 3B illustrates the housing cap of FIG. 3A and a spectrochrome housing, according to an example embodiment in both decoupled and assembled views.

Turning to FIG. 3B, in example embodiments, spectrochrome housing 310 may include one or more magnets 312, one or more of which may comprise one or more of the following substances: (i) neodymium magnets (including neodymium iron boron ("NdFeB") magnets), (ii) ceramic magnets, (iii) ferrite magnets, (iv) samarium cobalt ("SmCo") magnets, (v) alnico magnets, and/or combinations thereof. Other examples are possible. Although not illustrated in FIG. 3B, these magnets can also be attached in a manner causing the generation of a current through an electromagnetic coil, potentially through the interaction of the magnetic fields of the one or more magnets in the recess 302 of the housing cap 300 and the magnetic fields of the one or more magnets 312 in the spectrochrome housing 300. In some examples, this interaction may include manipulating (e.g. rotating) the housing cap 300 (and therefor magnet recess 302), and any substances contained in receiving portion 304, when the housing cap 300 is moved relative to the spectrochrome housing 310.

In some embodiments, as illustrated in FIG. 3B, the end of housing cap 300 may be closed and configured to hold one or more substances in the internal portion 304, as the spectrochrome housing 310 is inserted into the housing cap 300. Such substances may comprise one or more of the following: (i) water, (ii) gemstones, (iii) essential oils, (iv) salts, (v) homeopathic substances and remedies, (vi) pharmaceuticals, (vii) natural substances and/or combinations thereof, among other substances. Other examples are possible. In example embodiments, the housing cap 300 may be configured to secure to the spectrochrome housing 300 such that light is emitted via the end of the housing cap 300, thereby passing through and interacting with the one or more substances in the internal portion 304, and is substantially aligned to pass through the housing cap in one or more directions. Other examples are possible.

II. Example Variations

Although some of the acts and/or functions described in this disclosure have been described as being performed by a particular entity, the acts and/or functions can be performed by any entity, such as those entities described in this disclosure. Further, although the acts and/or functions have been recited in a particular order, the acts and/or functions need not be performed in the order recited. However, in some instances, it can be desired to perform the acts and/or functions in the order recited. Further, each of the acts and/or functions can be performed responsive to one or more of the other acts and/or functions. Also, not all of the acts and/or functions need to be performed to achieve one or more of the benefits provided by this disclosure, and therefore not all of the acts and/or functions are required.

Although certain variations have been discussed in connection with one or more examples of this disclosure, these variations can also be applied to all of the other examples of this disclosure as well.

Although select examples of this disclosure have been described, alterations and permutations of these examples will be apparent to those of ordinary skill in the art. Other changes, substitutions, and/or alterations are also possible without departing from the invention in its broader aspects as set forth in the following claims.

I claim:

1. A handheld device for providing a spectrochrome output, wherein the handheld device comprises:
   an enclosed chamber containing one or more substances;
   a light source;
   an electromagnetic coil;
   one or more magnets; and
   a housing, wherein the housing is configured to:
      (i) secure the enclosed chamber;
      (ii) secure the light source such that an output of the light source is substantially aligned to pass through the enclosed chamber in one or more directions; and
      (iii) secure the electromagnetic coil and the one or more magnets around the enclosed chamber such that an electromagnetic field is created in a substantially same direction of the output of the light source through the enclosed chamber.

2. The handheld device of claim 1, wherein the enclosed chamber containing one or more substances comprises an enclosed chamber of one or more noble gases.

3. The handheld device of claim 2, wherein the one or more noble gases comprise one or more of the following: (i) helium; (ii) neon; (iii) argon; (iv) krypton; (v) xenon; and (vi) radon.

4. The handheld device of claim 1, wherein the light source comprises a laser.

5. The handheld device of claim 4, wherein the laser comprises a laser with a wavelength between approximately 520 to 570 nanometers and a visible output of green light.

6. The handheld device of claim 4, wherein the laser comprises a laser with a wavelength of approximately 380 to 450 nanometers and a visible output of violet light.

7. The handheld device of claim 4, wherein the laser comprises a laser with a wavelength between approximately 450 to 495 nanometers and a visible output of blue light.

8. The handheld device of claim 4, wherein the laser comprises a laser with a wavelength between approximately 495 to 520 nanometers and a visible output of cyan light.

9. The handheld device of claim 4, wherein the laser comprises a laser with a wavelength between approximately 570 to 590 nanometers and a visible output of yellow light.

10. The handheld device of claim 4, wherein the laser comprises a laser with a wavelength between approximately 590 to 620 nanometers and a visible output of orange light.

11. The handheld device of claim 4, wherein the laser comprises a laser with a wavelength between approximately 620 to 740 nanometers and a visible output of red light.

12. The handheld device of claim 1, wherein the electromagnetic coil is secured around the enclosed chamber such that the electromagnetic field is created in a substantially same axial direction of the substantially aligned output of the light source through the enclosed chamber.

13. The handheld device of claim 1, wherein the housing comprises a recess to align the electromagnetic coil and the one or more magnets around the enclosed chamber such that the electromagnetic field is created in a substantially same axial direction of the substantially aligned output of the light source through the enclosed chamber.

14. The handheld device of claim 1, wherein the electromagnetic coil comprises a continuous strand of wire wrapped uniformly around a portion of the housing containing the enclosed chamber such that the electromagnetic field created by the electromagnetic coil is focused on an area in the enclosed chamber.

15. The handheld device of claim 14, wherein the electromagnetic coil comprises a copper wire.

16. The handheld device of claim 14, wherein the electromagnetic coil comprises a wire comprises one or more of the following materials: (i) silver; (ii) gold; (iii) aluminum; or (iv) iron.

17. The handheld device of claim 14, wherein the electromagnetic coil is connected to a first magnet of the one or more magnets at a first end of the continuous strand of wire and connected to a second magnet of the one or more magnets at a second end of the continuous strand of wire, and wherein the first and second magnet are securely contained in at least one additional recess of the housing.

18. The handheld device of claim 14, wherein the electromagnetic coil further comprises a first battery connected to a first end of the continuous strand of wire a and a second battery connected to a second end of the continuous strand of wire, and wherein the first and second battery are securely contained in at least one additional recess of the housing.

19. The handheld device of claim 1, wherein the one or more magnets comprise a neodymium magnet.

20. The handheld device of claim 1, wherein the housing is further configured to:
(i) receive the light source; and
(ii) after receiving the light source, activate the light source by turning the light source in a clockwise manner in relation to the housing.

21. The handheld device of claim 1, wherein the handheld device further comprises a housing cap configured to integrate with the housing and contain at least one or more of the following: (i) one or more additional substances; and (ii) one or more additional magnets.

* * * * *